(12) United States Patent
Gunther

(10) Patent No.: US 11,048,704 B2
(45) Date of Patent: *Jun. 29, 2021

(54) SYSTEM AND METHOD FOR INTEGRATING HEALTH INFORMATION SOURCES

(71) Applicant: Jeffrey M. Gunther, Crozet, VA (US)

(72) Inventor: Jeffrey M. Gunther, Crozet, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/780,587

(22) Filed: Feb. 3, 2020

(65) Prior Publication Data

US 2020/0167358 A1    May 28, 2020

Related U.S. Application Data

(63) Continuation of application No. 16/364,448, filed on Mar. 26, 2019, now Pat. No. 10,572,481.

(Continued)

(51) Int. Cl.
*G06F 16/2453* (2019.01)
*G16H 10/60* (2018.01)
*G06F 16/27* (2019.01)

(52) U.S. Cl.
CPC ........ *G06F 16/24542* (2019.01); *G06F 16/27* (2019.01); *G16H 10/60* (2018.01)

(58) Field of Classification Search
CPC ............... G06F 16/2452; G06F 16/951; G06F 16/9535; G06F 16/3322; G06F 16/3325; G06F 16/2453; G06F 16/24534; G06F 16/2457; G06F 16/3329; G06F 16/90324; G06F 16/242; G06F 16/243; G06F 16/285; G06F 16/00; G06F 16/2425; G06F 16/244; G06F 16/245; G06F 16/2455; G06F 16/283; G06F 16/313; G06F 16/3338; G06F 16/334; G06F 16/353; G06F 16/9032; G06F 16/90335; G06F 16/9574; G06F 3/1256; G06F 16/219; G06F 16/24524;

(Continued)

(56) References Cited

U.S. PATENT DOCUMENTS 5,301,317 A * 4/1994 Lohman ............ G06F 16/24547
6,347,329 B1    2/2002 Evans (Continued)

FOREIGN PATENT DOCUMENTS

CA       2637574 C       7/2007
WO   WO2001089363 A2   11/2001

*Primary Examiner* — Sheree N Brown

(57) ABSTRACT

The present invention provides a system and method for integrating multiple health information sources across a distributed computing environment to optimize the retrieval of data from a plurality of health information sources. The method and system includes receiving, in a leader node, a query request from a client device. The leader node can be any available node within the multiple of nodes. The method and system includes the leader node receiving a list of search nodes for conducting the query request and generating a search routine for executing the query request via the search nodes. The method and system includes executing the search operations based on the search routine, retrieving search data by accessing each of the health information sources via the coupled search nodes. The leader node receives the search data, integrating the search data and transmitting the combined search data to the client device.

15 Claims, 4 Drawing Sheets

Related U.S. Application Data

(60) Provisional application No. 62/761,465, filed on Mar. 26, 2018.

(58) Field of Classification Search
CPC ............ G06F 16/24575; G06F 16/248; G06F 16/332; G06F 16/3344; G06F 16/3349; G06F 16/337; G06F 16/58; G06F 16/90328; G06F 16/9537; G06F 16/955; G06F 16/9558; G06F 16/9566; G06F 16/972; G06F 17/211; G06F 17/2247; G06F 17/28; G06F 16/144; G06F 16/16; G06F 16/162; G06F 16/20; G06F 16/2228; G06F 16/2358; G06F 16/2428; G06F 16/2433; G06F 16/24522; G06F 16/24535; G06F 16/24539; G06F 16/24547; G06F 16/24553; G06F 16/2456; G06F 16/24568; G06F 16/24573; G06F 16/24578; G06F 16/2465; G06F 16/2474; G06F 16/2477; G06F 16/25; G06F 16/252; G06F 16/29; G06F 16/31; G06F 16/3323; G06F 16/3326; G06F 16/36; G06F 16/367; G06F 16/433; G06F 16/435; G06F 16/4393; G06F 16/48; G06F 16/583; G06F 16/686; G06F 16/7867; G06F 16/9024; G06F 16/93; G06F 16/954; G06F 16/957; G06F 16/958; G06F 17/21; G06F 17/212; G06F 17/218; G06F 17/2217; G06F 17/2294; G06F 17/243; G06F 17/248; G06F 17/27; G06F 17/2705; G06F 17/276; G06F 17/2795; G06F 3/0237; G06F 3/0484; G06F 3/167; G06F 8/60; G06F 9/445
USPC ........................................................ 707/768
See application file for complete search history.

(56) References Cited

U.S. PATENT DOCUMENTS

| | | | |
|---|---|---|---|
| 7,752,035 | B2 | 7/2010 | Oon |
| 8,260,635 | B2 | 9/2012 | Hasan et al. |
| 8,583,694 | B2 | 11/2013 | Siegel et al. |
| 8,650,045 | B2 | 2/2014 | Baldock et al. |
| 8,850,057 | B2 | 9/2014 | Natoli et al. |
| 9,996,664 | B2 | 6/2018 | Lloyd et al. |
| 10,629,310 | B2 * | 4/2020 | Livesay ................ H04L 67/12 |
| 2001/0041991 | A1 | 11/2001 | Segal et al. |
| 2001/0053986 | A1 | 12/2001 | Dick |
| 2003/0120515 | A1 | 6/2003 | Geller |
| 2003/0130867 | A1 * | 7/2003 | Coelho ................ G16H 20/10 705/2 |
| 2005/0278368 | A1 * | 12/2005 | Benedikt ............... G06F 16/84 |
| 2006/0277215 | A1 | 12/2006 | Siegel |
| 2006/0287890 | A1 | 12/2006 | Stead et al. |
| 2007/0203754 | A1 * | 8/2007 | Harrington ........... G06Q 50/22 705/3 |
| 2008/0046292 | A1 | 2/2008 | Myers et al. |
| 2008/0104104 | A1 * | 5/2008 | Nolan .................... G06F 16/93 |
| 2008/0104615 | A1 * | 5/2008 | Nolan ................... G16H 10/60 719/328 |
| 2008/0215627 | A1 | 9/2008 | Higgins et al. |
| 2008/0307430 | A1 | 12/2008 | Friedlander et al. |
| 2009/0222283 | A1 | 9/2009 | Lassetter et al. |
| 2011/0060757 | A1 * | 3/2011 | Dettinger ............. G16H 10/60 707/769 |
| 2011/0106564 | A1 | 5/2011 | Hachmeister et al. |
| 2013/0030838 | A1 | 1/2013 | Myers et al. |
| 2013/0110547 | A1 * | 5/2013 | Englund ............... G16H 10/60 705/3 |
| 2016/0063209 | A1 | 3/2016 | Malaviya |
| 2017/0161435 | A1 | 6/2017 | Orosco et al. |
| 2019/0198181 | A1 * | 6/2019 | Livesay ................ G16H 80/00 |

* cited by examiner

SYSTEM AND METHOD FOR INTEGRATING HEALTH INFORMATION SOURCES

RELATED APPLICATIONS

The present application is a continuation of, and claims priority to, U.S. patent application Ser. No. 16/364,448 filed Mar. 26, 2019, which relates to and claims priority to U.S. Provisional Application Ser. No. 62/761,465 filed Mar. 26, 2018, the disclosure of which is incorporated by reference herein, as well as relates to.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent files or records, but otherwise reserves all copyright rights whatsoever.

FIELD OF INVENTION

The present invention relates generally to health information management more specifically to logically integrating a plurality of disparate health information sources for data query operations.

BACKGROUND

Healthcare delivery organizations are grappling with a growing number of challenges, including needing to become more efficient, reduce operational costs, improve patient experiences and health outcomes, and innovate in the way they provide care. With the adoption of electronic healthcare records nearing completion and the need to establish population health management programs, these healthcare delivery organizations are now seeking to transform their organizations into competitive digital businesses that demonstrate acute situational awareness and operational excellence across the entire healthcare continuum.

Existing approaches leveraged by healthcare delivery organizations to measure and monitor organizational performance focus on a strategy of building a physical implementation of a data consolidation process across a plurality of health information sources. These multiple, disparate, health information sources provide for a diverse amount of healthcare data and patient information being scattered across many different systems running on various operating systems across disparate networks, even within a single healthcare delivery organization.

Implementing a data consolidation strategy requires extracting, transforming, and loading large amounts of data scattered across disparate health information systems into a centralized repository with a unified data model. This technical approach requires healthcare delivery organizations to create, operate and maintain a data pipeline from every existing healthcare information source for subsequent loading on a regular interval into a centralized repository.

Since each health information source uses different data types and formats, healthcare delivery organizations must resolve a series of data compatibility issues before any raw data can be used for consolidated reporting.

The use of a unified data model within a centralized repository requires transforming the raw data as extracted from health information sources into an intermediate form that is significantly less flexible.

Any addition or changes to the unified data model requires healthcare delivery organizations to modify all data pipelines, transformation logic and reprocess data all while not impacting existing business operations.

Scaling a data consolidation strategy into a system-wide operation across an entire healthcare delivery organization with many multiple health information sources across various operating systems, consolidated organizational performance reporting often evolves into an untenable proposition. These complications in meaningfully and timely leveraging diverse health information sources, create operational inefficiencies and ultimately impact patient care.

Therefore, there exists a need for improved data integration relating to integrating disparate health information sources across the continuum of care.

BRIEF DESCRIPTION

The present invention provides a system and method for integrating multiple health information sources across a distributed computing environment. The health information sources can be disparate healthcare information systems.

The method and system includes one or more health information sources having health information stored therein. For each of these sources, a node is associated therewith. The node performs processing operations facilitating the improved query operations.

The method and system includes receiving, in a leader node, a query request from a client device. The query request is a computer-implemented request for seeking health information from one or more of the health information sources. The leader node can be any available node within the multiple of nodes.

The method and system includes the leader node receiving a list of search nodes for conducting the query request. Each of the search nodes is associated with a health information source having data stored therein searchable by the query request. The leader node may be a node having processing availability and does not have to be a node directly associated with a health information source searchable with the query request.

The method and system includes generating a search routine for executing the query request via the search nodes. The search routine may include instructions for conducting the search, such as health information source-specific information, sequential instructions, etc.

The method and system includes executing the search operations based on the search routine, retrieving search data by accessing each of the health information sources via the coupled search nodes.

The method and system includes receiving, in the leader node, the search data from the search nodes and transmitting the search data to the client device. Therein, the method and system allows for improved searching of a plurality of disparate health information systems by utilizing a leader node and multiple search nodes.

In one embodiment, the method and system includes parsing the query request to generate a logical query plan. Whereby, the method and system transforms the logical query plan using a plurality of custom rules to generate a physical query plan. The physical query plan is a computationally-expressed description of the physical operations to be performed by one or more execution engines.

Nodes may additionally include local memory for storing previously-retrieved search data for optimizing search functions, such that the physical query plan can account for this is locally-stored data.

The method and system includes executing searching operations using the physical query plan. The search nodes perform these searching operations. The searching operations retrieve search data from the associated health information source, either directly from the system's storage interface or via the local memory in or associated with the node.

In one embodiment, the selection of the search nodes may be performed using a curator. The curator may be external to the leader node. The total compendium of nodes can also be known as an ensemble.

Thereby, the method and system improves access and efficiencies associated with integrating various healthcare and related information stored in disparate health information sources using techniques and processing operations described herein. The present method and system improves searching efficiencies by utilizing search nodes ahead of the health information sources, as well as facilitating the searching request via the leader node.

A better understanding of the disclosed technology will be obtained from the following detailed description of the preferred embodiments taken in conjunction with the drawings and the attached claims.

DETAILED DESCRIPTION

Figure 1:
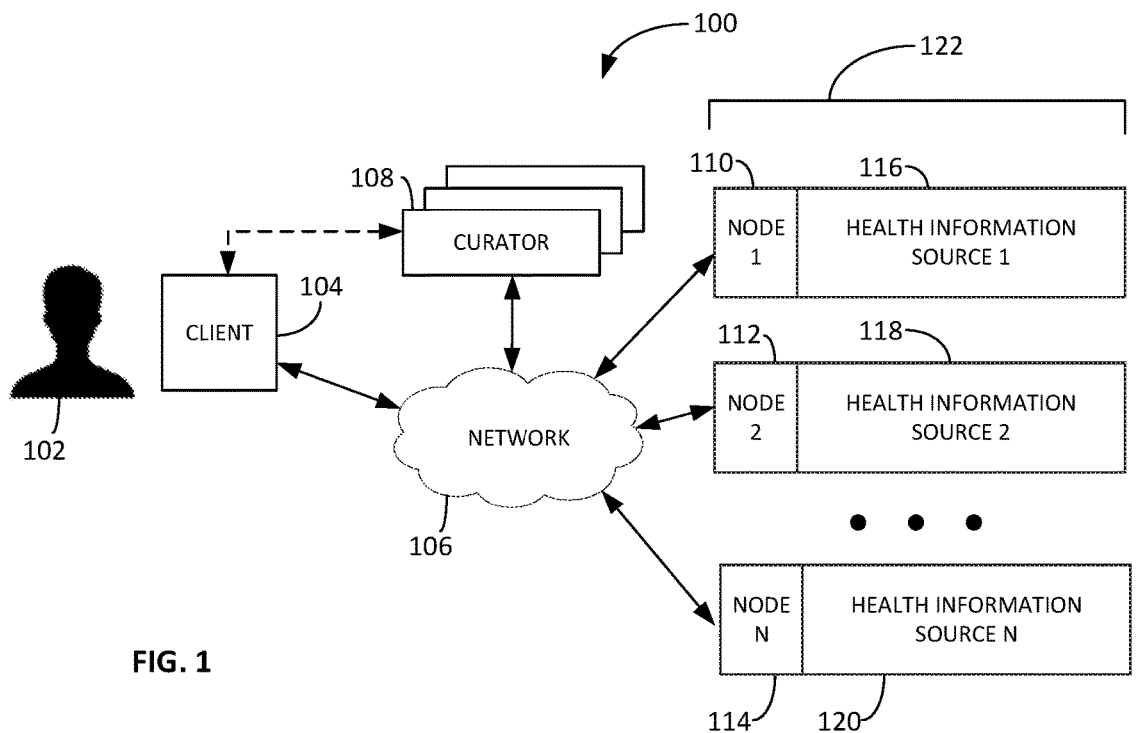
FIG. 1 illustrates a system diagram of a computing system providing for integrating health data across a plurality of disparate health information sources.

FIG. 1 illustrates one embodiment of a system 100 providing for accessing health data across a plurality of health information sources. The system 100 is accessible by an end user 102. The system 100 includes a client device 104, a network 106, curators 108, a first node 110, a second node 112 and an Nth node 114, where N is any suitable integer. The system 100 further includes a first health information source 116, a second health information source 118 and an Nth health information source 120.

The end user 102 may be any suitable user or users accessing the present method and system for search health data. The end user 102 is not expressly limited to a user, but can be another computing system or processing device or machine operative to engage the client device as described herein. The client device 104 may be any suitable type of processing device or devices operative to provides functional operations as described herein. For example, the client device 104 may be a computer running a software application thereon, including such as a laptop or desktop computer running a locally-based application. In another example, the client device 104 may be a local computer running a browser or other portal-type application with executable(s) running on a server (not illustrated). The client device 104 may be a stand-alone computer, part of a network of computers, a portable computing device such as a tablet computer, mobile phone, or any other suitable computing device. Whereby, the client device 104 provides for end user 102 interaction for performance of processing operations described herein.

In one embodiment, the client device 104 may include functionality via networks or cloud computing. For example, the client device 104 may execute on a local window providing user interface access to a cloud-based application for conducting searching operations as noted herein.

The network 106 may be any suitable network or combination of networks providing for communication thereacross. For example, the network 106 may be the Internet, an intranet, a combination of networks such as a mobile or cellular network connecting to another network, etc. In one example, the network 106 may be the Internet including appropriate security protocols for transmissions thereacross. In another example, the network 106 may be a private corporate intranet with health information sources securely networked therethrough.

The curator 108 may be disposed on a network location or associated with the client device 104. In one embodiment, the curators operate on the same network as the clients and nodes. For example, where functionality exists in cloud-based or networked-based processing environment(s), the curator 108 may be incorporated in these environment(s). The functional operations of the curator 108 provide support for the searching operations, as noted below In one embodiment, the curator 108 allows for improvement of the search operation by selecting or proposing the health information sources for search operations. For example, an ensemble 122 may include a large number of health information sources, the curator 108 including connectivity specifications or reference indicators for the type and value of information stored in these different sources. Therefore, one embodiment may include the curator 108 determining the health information sources 116-120 for conducting the search operation. Moreover, FIG. 1 illustrates a plurality of curators 108, it is recognized that multiple curators 108 may be utilized for fault tolerance purposes, such as including any odd number of curators.

The nodes 110, 112, and 114 are processing operations performed on one or more computing devices in a central or distributed fashion. Each node in the ensemble 122 is connected to at least one health information source. In one embodiment, each of the nodes 110, 112, and 114 are executable operations performed by one or more processing devices associated with corresponding health information sources 116, 118, and 120. Whereas, in alternative embodiments, the nodes 110, 112, and/or 114 may be distributed or located external to the health information sources 116, 118, and 120.

The health information sources 116, 118, and 120 are one or more information system and/or processing systems associated with or containing health or health-related information. By way of example, the health information source may be a patient record system, a medical billing system, a facilities management system, a medical device located in a patient's home or any other suitable data system that provides health or health-related information.

The health information sources include data stored therein, as well as one or more computing devices controlling access to the data. Moreover, while illustrated as separate health information sources 116, 118, 120, it is recognized these sources may be in a networked or distributed environment, such as data stored in a cloud environment, locally stored in a data or server facility, or combination thereof. The health information sources 116, 118, and 120 store health information or health-related information usable by healthcare delivery organizations during the ordinary course of operation, whereby the present method and system accesses these systems for query operations as described herein.

Figure 2:
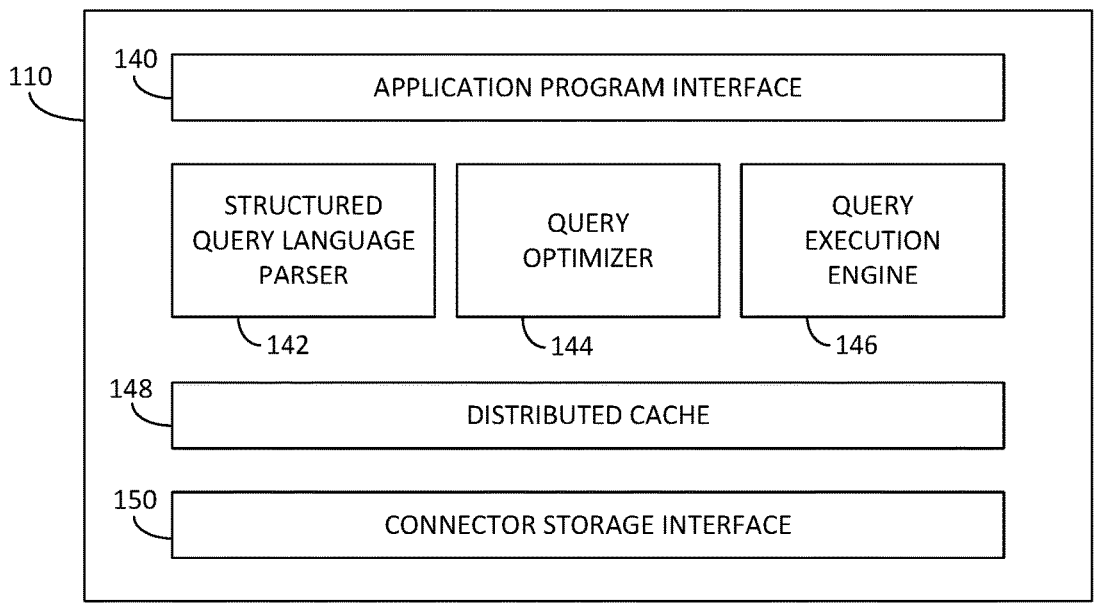
FIG. 2 illustrates a block diagram of one embodiment of a node.

FIG. 2 illustrates one embodiment of a node 110. It is recognized the node 110 may be any node, such as nodes 112, 114. The node 110, in one embodiment, is connected to or part of the health information sources 116. The node 110 may be part of a computing processing network providing operational features in response to executable instructions in a central or networked computing environment. The node 110 includes an application program interface (API) 140. The node 110 further includes query analysis and modification engines, a structured query language parser 142, a query optimizer 144, and a query execution engine 146. The node 110 includes distributed cache 148, as well as a connector storage interface 150.

The API 140 is a software component of the node 110 providing for interfacing between the client device 104, the curator 108, any node, such as nodes 112, 114, or other network-based communication devices and the health information system. The API 140 may be composed of standard program encoding including functionality for receiving the query requests, as well as providing for operations with the query analysis and modification engines.

The structured query language parser 142 operates to parse an incoming query request, applying custom rules to convert specific query operators into a specific logical operator syntax. The logical operators form a logical query plan, which describes the workload and information being sought by the multiple health information systems. The logical query plan can also describe which of the health information systems are usable for determining search result information.

In one embodiment, the logical query plan includes instructions for general searching operations, such as data field retrieval operations for the associated health information sources. By way of example, the logical query plan can include instructions for retrieving zip code information associated with specific patients from two designated sources and then also retrieving gender information associated with those patients.

The query optimizer 144 operates in response to executable instructions for optimizing the ordering of query operators of the logical query plan. The query optimizer 144 applies various types of rules to rearrange query operators and query functions into an optimal query plan. The query optimizer 144 converts the optimal query plan into a physical plan that describes how to execute the query across the health information sources.

In one embodiment, the physical query plan includes designated execution instructions for the physical access and retrieval. Using the above example, where the logical query plan is zip code and gender data, the physical query plan may include searching the first health information source, searching the second health information, sending data to a leader node, and the leader node performing a munging operation thereon.

The query execution engine 146, in response to executable instructions, performs the query operations, both in the node 110 as well as in other connected nodes, such as nodes 112, 114 of FIG. 1. The distributed cache 148 is a memory location operative for storing search results therein.

The connector storage interface 150 is a processing module for engaging with the health information system. In one embodiment, the connector storage interface 150 uses standard interfacing operations such as not requiring specific knowledge of specific data encoding within the connected health information system.

The connector storage interface 150 further provides for managing metadata associated with the health information source. As noted herein, a common hurdle to multi-system searching and data mining exists due to differences or discrepancies between data and meta-data. For example, a zip code may be a 5 digit code in one system and a 5+4 code in another. Via the connector storage interface 150, the variations in meta-data differences can be minimized.

As described herein, one or more processing devices perform processing operations in response to executable instructions. The executable instructions may be software code or other types of instructions readable by one or more processing device, stored in one or more computer readable mediums, such as non-transitory medium, including for example one or more data storage devices. The data storage devices may be centrally located or can be accessible in a distributed environment, as recognized by one skilled in the art.

Figure 3:
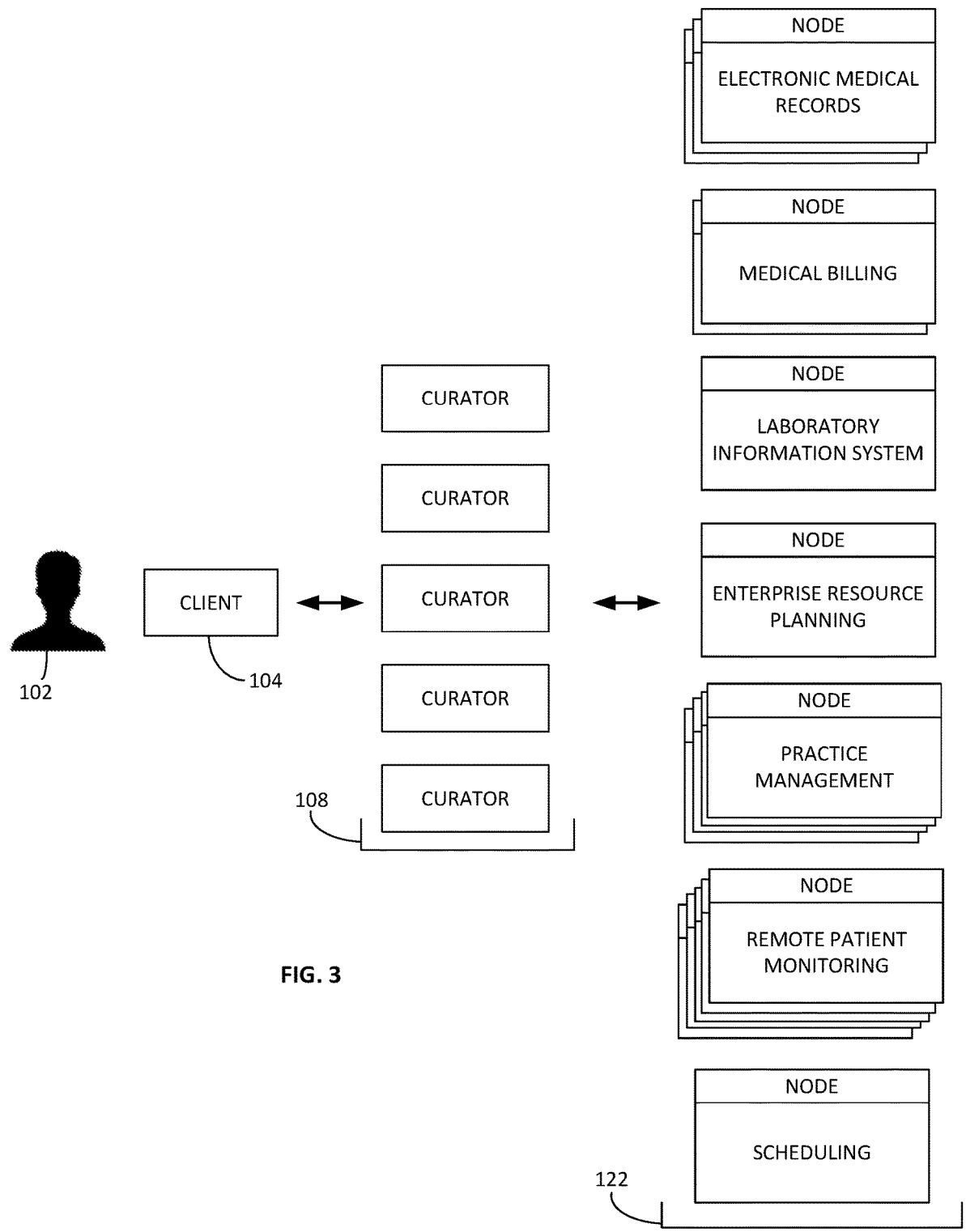
FIG. 3 illustrates a generalized system diagram of the data searching environment with multiple health information sources.

FIG. 3 illustrates a more generalized view of the processing environment of the present method and system. Similar to FIG. 1, the end user 102, using a computing device, such as client device 104 performs a search operation. As recognized by one skilled in the art, the generalized representation of FIG. 3 omits many elements usable for performing the searching operations, including network connectivity and any intermediate processing servers or systems. The networked interoperability and communication is in accordance with known techniques.

The client device 104, receiving a query request, accesses a curator 108. FIG. 3 recognizes that the system may include any number of curators. The operation of the curator is to recognize the ensemble 122 of available health information sources, as well as indicating which sources in the ensemble will perform a searching operation.

In the FIG. 3 example, the ensemble includes a wide variety of health information sources. Each source includes a node associated therewith. While not an exhaustive or limiting list of types of health information sources, the exemplary ensemble 122 includes: multiple electronic medical record (EMR) systems, two medical billing systems, a laboratory information system (LIS), an enterprise resource planning (ERP) system, multiple practice management systems, multiple remote patient monitoring devices, and a patient scheduling system.

For example, the EMR systems can be from a variety of facilities across multiple geographic locations. In the example of a hospital or health care management company having multiple facilities across a large geographic area, those facilities may each have individual systems for storing patient records. Similarly, where multiple nested systems are illustrated, this can represent multiple disparate systems of the same type.

For example, the LIS can represent an informatics system that processes, stores and manages data from all stages of medical processes and tests. For example, the remote patient monitoring system could be used by healthcare delivery organizations to monitor and manage patient populations with chronic conditions outside of conventional clinical settings. Other noted systems, medical billing systems, laboratory information systems, enterprise resource planning systems, practice management systems, and scheduling systems are consistent with systems as recognized by one skilled in the art.

Figure 4:
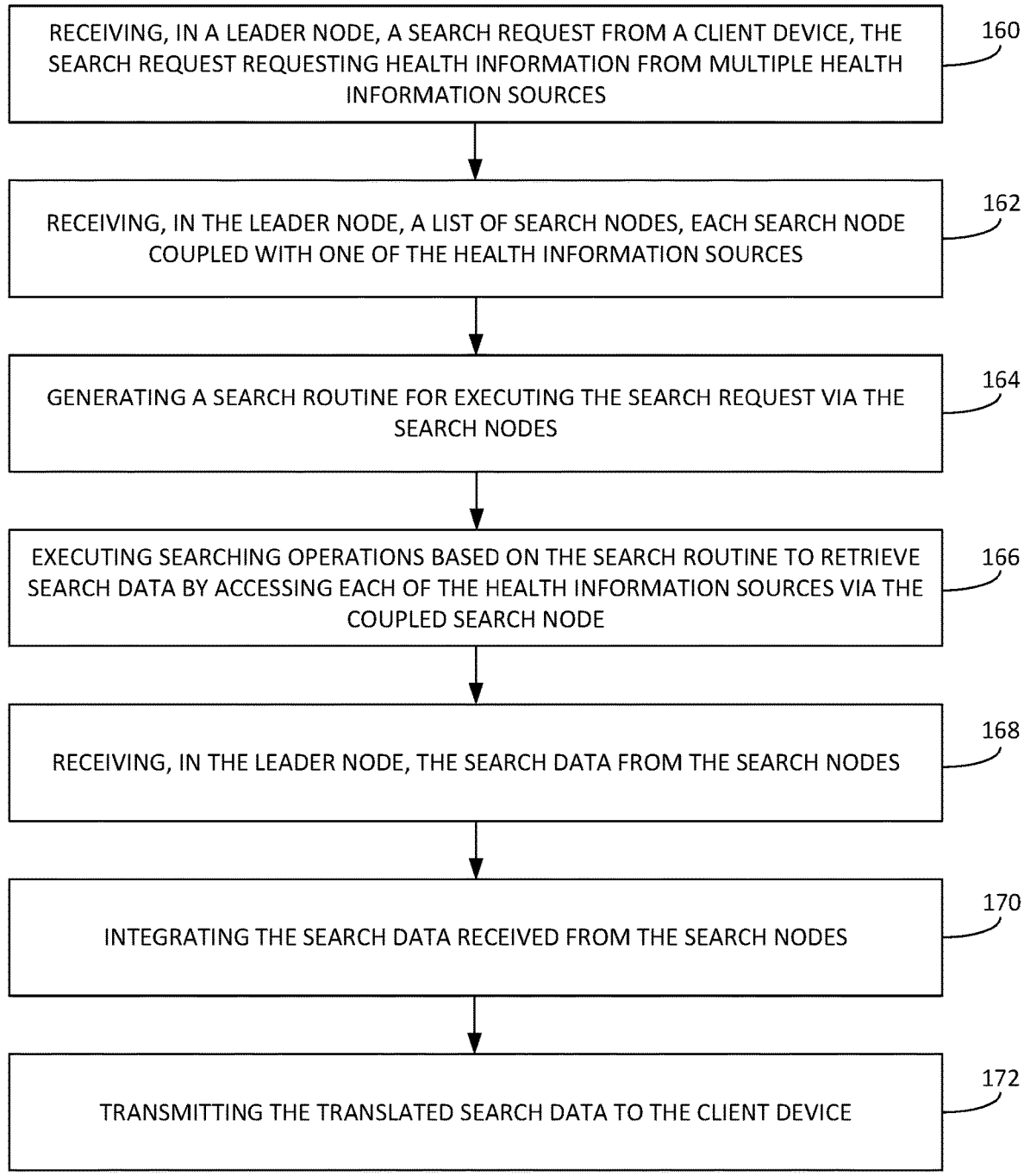
FIG. 4 illustrates a flow chart of the steps of one embodiment of a method for integrating health data across a plurality of health information sources.

FIG. 4 illustrates a flowchart of the steps for one embodiment of a method for accessing health data across a plurality of health information sources.

Step 160 is receiving a query request from a client device, the query request requesting health information from multiple sources. In step 160, the query request is received in a leader node. From a terminology perspective, the leader node is designated to process the query request. The leader node can be determined based on availability and the leader node does not necessarily have to be associated with a health information source being searched.

The general method can operate by a leader node requesting leader node status, such as being available to process the query request, or the leader node can be selected by the curator. Thus, when some nodes are active in performing operations, other nodes having available processing bandwidth can undertake being the leader node to facilitate the search in a timely manner.

With respect to FIG. 1, the client device 104 generates the data query request, such as in response to input from end user 102. The request can be formatted in accordance with known remote procedure call (RPC) protocols. Whereas, any suitable protocol as recognized by one skilled in the art may be used and the present method is not specifically restricted to using the RPC protocols.

Step 162 is receiving, in the leader node, a list of search nodes, each of the search nodes coupled with health information sources. In one embodiment, the curator, with knowledge of the nodes and sources in the ensemble, selects the search nodes based on the search operation, each selected search node coupled to a health information source designated for data retrieval operations.

Step 164 is generating a search routine for executing the query request via the search nodes. As described in greater detail below, the search routine includes optimization routines for efficiently performing the searching across multiple sources via the associated nodes.

For example, step 164 may be performed by the query optimizer 144 within the node 110 of FIG. 2. Similarly, the API 140 of FIG. 2 may perform further query request transformations, allowing for format usable by the health information sources 116 of FIG. 1.

Step 166 is executing searching operations based on the search routine to retrieve search data by accessing each of the health information sources via the coupled search nodes. With reference to FIG. 1, leader node, such a node 110 can then access health information sources 118 and 120 via nodes 112 and 114, respectively.

Step 168 is receiving, in the leader node, the search data from the search nodes. In this case, the search data can be all of the search data or can be partial. In the example of a physical query plan directing segmental searching, the search data can be data from a first search segment and then later, data from a second search segment sent later.

Step 170 is translating the search data received from the search nodes. In one embodiment, step 170 is performed in the leader node. The leader node may perform additional processing steps as part of the translation. For example, the leader node may mung the multiple data sets, translate the search data from a raw data format into a usable format. The munging of data may be part of the physical query plan.

Step 172 is transmitting the translated search data to the client device. Thereby, the method and system generates improved searching operations across disparate health information sources using a leader node and search nodes, as well as the search routine from the query request.

In one embodiment, generating the search routine includes generating a logical query plan and then generating a physical query plan. The logical query plan designating searching operations to be performed in multiple sources and the physical query plan designated search and data result transmission sequencing.

Figure 5:
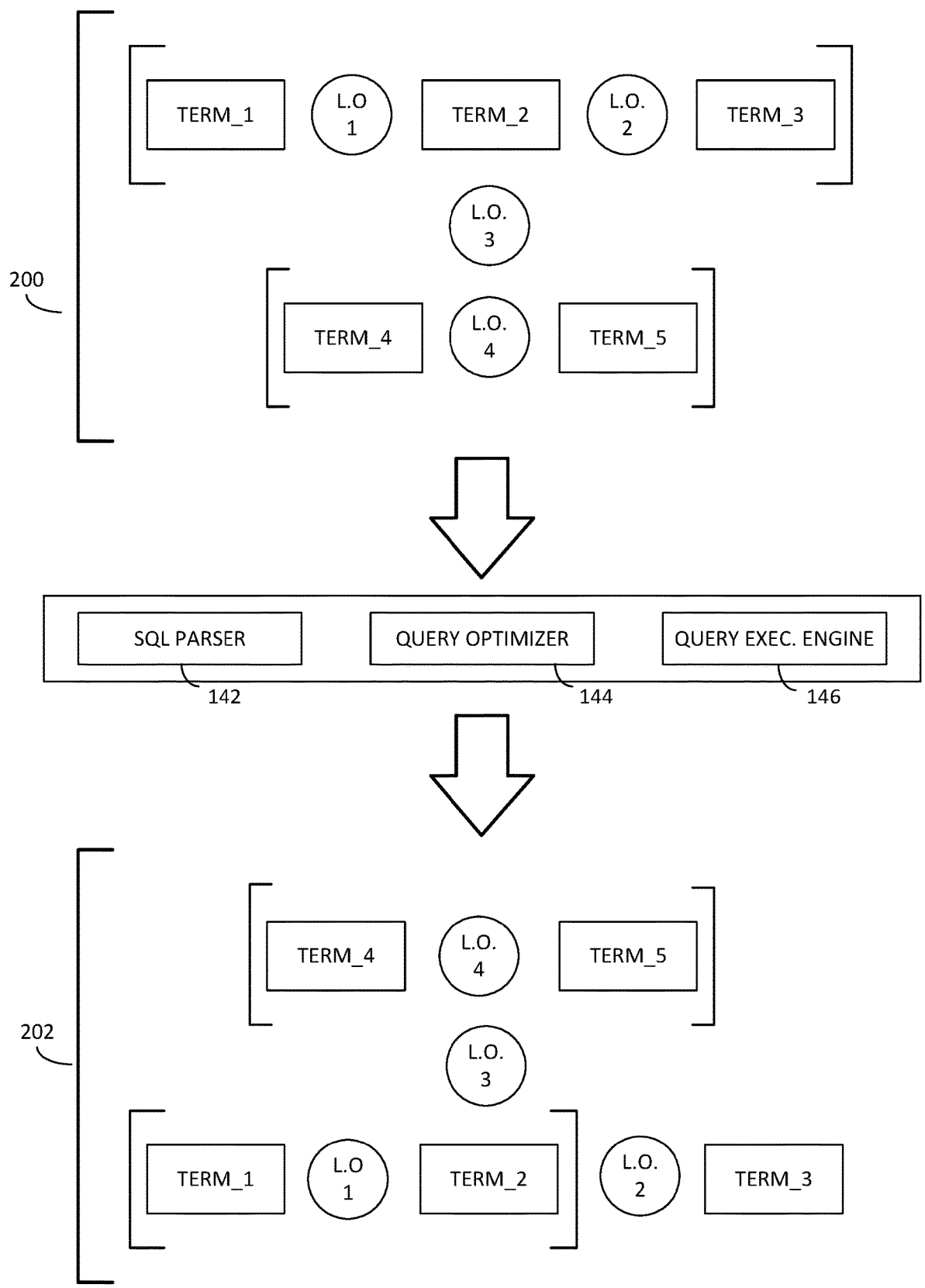
FIG. 5 illustrates a graphical representation of one embodiment of a modification of a query request.

The search routine generation can include parsing the query request to generate a logical query plan. By way of example, FIG. 5 illustrates an example of parsing the search routine as performed by the leader node. For generating the physical query, the method and system includes translating the logical query plan using custom rules. These custom rules apply to not only the search, but also to the type of data being retrieved for operational efficiency. Application of custom rules is further noted in the exemplary search noted below.

The logical query plan, parsed from the query request, designates search fields for the health information sources. The physical query plan designates search operation sequences for searching the health information sources.

In one embodiment, the physical query plan can be further revised and optimized for execution across the health information sources, such as taking into account source and data accessibility and efficiency factors. For example, if one source or node is under a heavy processing load, the search may delay or otherwise optimize other searching functions.

In another example, a node may include previously-accessed data in a distributed cache (see distributed cache 148 of FIG. 2). Optimization may include reliance on search data available in a distributed cache, avoiding any delay associated with directly accessing the health information source.

In the leader node 110 of FIG. 2, the structured query language parser 142 parses the structured query language (SQL) query, applying custom rules to convert specific SQL operators into a specific logical operator syntax. The plurality of these logical operators form a logical query plan. The logical query plan describes the work required by the ensemble to generate the query results, as well as defining which health information systems to utilize.

The leader node 110 sends the logical query plan into the query optimizer 144 to optimize the order of SQL operators in a statement and read the logical query plan. The query optimizer 144 applies various types of rules to rearrange the SQL operators and SQL functions into an optimal query plan. The query optimizer 144 converts the optimal query plan into a physical plan for query execution.

For illustration purposes, FIG. 5 illustrates one embodiment of a generalized SQL query including the query request 200 consisting of multiple search terms of logical operators. As recognized by one skilled in the art, the query request 200 can include any number of terms and logical operators or conditional statements.

Via operational steps performed by the structured query language parser 142 and query optimizer 144, the query request 200 is modified into an optimal query plan 202. In this illustrated example, the optimal query plan 202 includes the reorganization of the terms and logical operators or conditional statements.

Not expressly illustrated, the optimal query plan 202 is then further translated into the physical plan for execution by the query execution engine 146. The query execution engine 146 therein executes the query via accessing multiple health information systems as described herein.

In one example, a user may request to search multiple health information sources for information regarding patient demographic information. The user may seek to designate multiple health information sources, or can generate a query request which is then analyzed for selecting appropriate sources.

In this example, the user can access a search operation via any number of manners, such as a command line query request, a web-based search portal, a dedicated locally-executing software application, etc. The query request can include information about not only zip code information for patients, but also patient gender. For example, the user may wish to see which genders in different geographic regions, designed by zip codes, have higher participation rates.

The query request, once submitted, is processed by the curator for determining appropriate search nodes. The query request can be sent to the ensemble with an available node accepting status as a leader node, and in another embodiment the leader node may be assigned.

With designated search nodes, the leader node processes the query request to generate the search routine.

In this example, if there are two search nodes, the logical query plan can designate that the first searches are searching zip code information from the first health information source and the second health information source. The logical query plan can then designate searching the gender field in both sources. The logical query plan can then designate translation of the zip code data based on the gender data.

Keeping the example of two search nodes, the logical query plan can then be translated to a physical query plan. This physical query plan can be first searching zip code and gender information in the first health information source, then searching zip code and gender information in the second health information source. The physical query plan then instructs sending the search data to the leader node and the leader node munging the search data based on the request to translate zip data based on the gender data.

Where step 168 of FIG. 4 above noted search segments, the present example could also include noted search segments. For example, the search for zip code information in the first source can be a first segment, searching for gender information in the first source can be a second segment and searching for zip and gender information in the second source can be a third segment. Thereby, the physical query plan can be further rendered based on these segments.

The rendering of segments provides for additional levels of processing optimization by accounting for system-wide or source-specific limitations. For example, factors affecting the optimization of the physical query plan can include factors relating to available resources, processing loads in the health information sources and data distribution limitations. For example, high network traffic may prohibit large data transfers at specific times or if data is locally stored in the nodes distributed cache, searching operations may be prioritized, or in another example if data translation or further searching operations are contingent upon other search factors, those first searches can be prioritized.

As noted above, the connector storage interface 150 of FIG. 1 can further assist in the searching, accounting for source-specific encoding and/or metadata. In the example of zip code data, the first source may use a five digit zip code and the second source a five+four zip code. Thus, the connector storage interface 150 can clip the extra four digits of the second source zip code data.

Therefore, the present method and system improves data access across a plurality of disparate health information sources by utilizing a node as well as query processing and optimizing techniques. Where prior techniques were slow and dealt with stale data sets, the inclusion of the search nodes and operations via the leader node allows timely access to health information from these disparate health information sources.

The present method and system provides a simplified technique for the analysis of structured and semi-structured information across disparate health information sources using an interactive, scalable, low-latency query engine to consolidate information in the absence of a centralized data repository. The method and system facilitates searching and data query operations by integrating data from disparate sources in a scalable and distributed manner, accessing disparate sources regardless of location or format sources employ to store its data.

Therein, in the face of ever-growing costs of healthcare, healthcare delivery organizations are asked to improve clinical and financial outcomes and address growing demand with limited resources, human or otherwise. The present method and system, by significantly reducing the expense required to integrate these disparate health information systems, brings together disconnected health information from across the entire continuum of care. Upon virtual combination of these disparate sources, healthcare delivery organizations are better positioned to make broad and quickly informed decisions for improving all aspects of healthcare.

FIGS. 1 through 5 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, Applicant does not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments so fully reveals the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein.

What is claimed is:
1. A system for health information integration, the system comprising:
at least one processing device, in response to executable instructions stored in a non-transitory computer-readable medium, operative to:

receive, in a leader node, a query request from a client device, the query request requesting health information from a plurality of health information sources, the health information sources being disparate from each other;

receive, in the leader node, a list of search nodes, each search node coupled with one of the plurality of health information sources;

generate a search routine for executing the query request via the search nodes including parsing the query request to generate a logical query plan and transforming the logical query plan using a plurality of custom rules to generate a physical query plan, the physical query plan designating searching operations;

execute the searching operations based on the search routine to retrieve search data by accessing each of the health information sources via the coupled search node, each of the coupled search nodes including a connector storage interface for managing metadata associated with the associated health information source;

receive, in the leader node, the search data from the search nodes;

integrate the search data received from the search nodes, wherein integrate, comprises: munging the search data to translate it from a raw data format into a usable format; and transmit the integrated search data to the client device.

2. The system of claim 1, wherein the logical query plan designates search fields for the health information sources associated with the search nodes and the physical query plan designates search operation sequences for searching the health information sources associated with the search nodes.

3. The system of claim 1, the processing device further operative to:

prior to executing the searching operations, optimize the physical query plan for execution across an ensemble.

4. The system of claim 3, the processing device further operative to:

detect, for each of the search nodes in the ensemble, a local memory device having previous search data stored therein, and optimize the physical query plan to account for any previous search data.

5. The system of claim 1, the processing device further operative to:

render the physical query plan into a plurality of search segments; and execute the searching operations using the plurality of search segments.

6. The system of claim 5, wherein the rendering of the physical query plan into a plurality of search segments is based on at least one of: resource availability factors, processing loads on the health information sources, and data distribution information.

7. The system of claim 1, wherein the query request is generated on the client device via at least one of: an application program interface and a command line.

8. A method for health information integration, the method comprising:

receiving, in a leader node, a query request from a client device, the query request requesting health information from a plurality of health information sources, the health information sources being disparate from each other;

receiving, in the leader node, a list of disparate search nodes, each search node coupled with one of the plurality of health information sources;

generating a search routine for executing the query request via the search nodes including parsing the query request to generate a logical query plan and transforming the logical query plan to generate a physical query plan, the physical query plan designating searching operation;

executing searching operations based on the search routine to retrieve search data by accessing each of the health information sources via the coupled search node, each of the coupled search nodes including a connector storage interface for managing metadata associated with the associated health information source;

receiving, in the leader node, the search data from the search nodes;

integrating the search data received from the search nodes, wherein integrate, comprises: munging the search data to translate it from a raw data format into a usable format; and transmitting the integrated search data to the client device.

9. The method of claim 8, wherein the logical query plan designates search fields for the health information sources associated with the search nodes and the physical query plan designates search operation sequences for searching the health information sources associated with the search nodes.

10. The method of claim 8 further comprising:

prior to executing the searching operations, optimizing the physical query plan for execution across an ensemble.

11. The method of claim 10 further comprising:

detecting, for each of the search nodes in the ensemble, a local memory device having previous search data stored therein, and optimizing the physical query plan to account for any previous search data.

12. The method of claim 8 further comprising:

rendering the physical query plan into a plurality of search segments; and executing the searching operations using the plurality of search segments.

13. The method of claim 12, wherein the rendering of the physical query plan into a plurality of search segments is based on at least one of: resource availability factors, processing loads on the health information sources, and data distribution information.

14. A method for health information searching, the method comprising:

receiving, in a leader node, a query request from a client device, the query request requesting health information from a plurality of health information sources, the health information sources being disparate from each other;

receiving, in the leader node, a list of search nodes, each search node coupled with one of the plurality of health information sources;

parsing the query request to generate a logical query plan;

transforming the logical query plan using a plurality of custom rules to generate a physical query plan, the physical query plan designating searching operations;

executing searching operations based on a search routine to retrieve search data by accessing each of the health information sources via the coupled search node, each of the coupled search nodes including a connector storage interface for managing metadata associated with the associated health information source;

receiving, in the leader node, the search data from the search nodes;

integrating the search data received from the search nodes, wherein integrate, comprises: munging the search data to translate it from a raw data format into a usable format; and transmitting the integrated search data to the client device.

15. The method of claim 14 further comprising:

detecting, for each of the search nodes, a local memory device having previous search data stored therein, and optimizing the physical query plan to account for any previous search data.

\* \* \* \* \*